United States Patent
Gil et al.

(10) Patent No.: US 8,147,547 B2
(45) Date of Patent: Apr. 3, 2012

(54) SPINAL IMPLANT

(75) Inventors: Carlos E. Gil, Collierville, TN (US);
Randall N. Allard, Germantown, TN (US); Gregory C. Marik, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1553 days.

(21) Appl. No.: 11/118,706

(22) Filed: Apr. 29, 2005

(65) Prior Publication Data

US 2006/0247774 A1 Nov. 2, 2006

(51) Int. Cl.
*A61F 2/44* (2006.01)
(52) U.S. Cl. .................................... 623/17.11
(58) Field of Classification Search .... 623/17.11–17.16; 606/246–279
See application file for complete search history.

(56) References Cited

U.S. PATENT DOCUMENTS

| | | | |
|---|---|---|---|
| 4,878,915 A * | 11/1989 | Brantigan | 623/17.11 |
| 4,961,740 A * | 10/1990 | Ray et al. | 606/247 |
| 5,015,247 A | 5/1991 | Michelson | |
| 5,133,765 A | 7/1992 | Cuilleron | |
| 5,171,313 A | 12/1992 | Salyer | |
| 5,171,324 A | 12/1992 | Campana et al. | |
| 5,409,492 A | 4/1995 | Jones et al. | |
| 5,476,466 A | 12/1995 | Barrette et al. | |
| 5,484,443 A | 1/1996 | Pascarella et al. | |
| 5,486,181 A | 1/1996 | Cohen et al. | |
| 5,489,308 A * | 2/1996 | Kuslich et al. | 623/17.11 |
| 5,702,463 A | 12/1997 | Pothier et al. | |
| 5,725,591 A | 3/1998 | DeCarlo, Jr. et al. | |
| 5,800,546 A | 9/1998 | Marik et al. | |
| 5,849,015 A | 12/1998 | Haywood et al. | |
| 5,895,427 A * | 4/1999 | Kuslich et al. | 128/898 |
| 5,951,564 A | 9/1999 | Schroder et al. | |
| 5,968,098 A * | 10/1999 | Winslow | 623/17.11 |
| 5,980,522 A * | 11/1999 | Koros et al. | 623/17.11 |
| 6,022,355 A | 2/2000 | Peche et al. | |
| 6,063,091 A | 5/2000 | Lombardo et al. | |
| 6,190,413 B1 | 2/2001 | Sutcliffe | |
| 6,319,257 B1 | 11/2001 | Carignan et al. | |
| 6,432,110 B1 | 8/2002 | Richelsoph | |
| 6,447,546 B1 * | 9/2002 | Bramlet et al. | 623/17.16 |
| 6,454,807 B1 * | 9/2002 | Jackson | 623/17.15 |
| 6,468,281 B1 | 10/2002 | Badorf et al. | |
| 6,471,724 B2 * | 10/2002 | Zdeblick et al. | 623/17.16 |
| 6,589,284 B1 | 7/2003 | Silberer | |
| 6,626,913 B1 | 9/2003 | McKinnon et al. | |
| 6,706,072 B2 | 3/2004 | Dwyer et al. | |
| 7,473,276 B2 * | 1/2009 | Aebi et al. | 623/17.15 |
| 7,503,933 B2 | 3/2009 | Michelson | |
| 7,618,460 B2 * | 11/2009 | Boyd | 623/17.16 |
| 7,621,958 B2 * | 11/2009 | Zdeblick et al. | 623/17.16 |
| 7,637,953 B2 * | 12/2009 | Branch et al. | 623/17.11 |
| 2002/0128715 A1 * | 9/2002 | Bryan et al. | 623/17.15 |
| 2003/0023305 A1 * | 1/2003 | McKay | 623/17.11 |
| 2004/0093083 A1 * | 5/2004 | Branch et al. | 623/17.11 |

(Continued)

FOREIGN PATENT DOCUMENTS

EP 0978258 A1 2/2000

(Continued)

*Primary Examiner* — Thomas C. Barrett
*Assistant Examiner* — Christopher Beccia

(57) ABSTRACT

Embodiments for a spinal implant having elements that are accessible by a surgical approach and releasably engagable by a surgical tool for improved revision of the spinal implant about a patient's spine.

9 Claims, 6 Drawing Sheets

U.S. PATENT DOCUMENTS

| | | | |
|---|---|---|---|
| 2004/0102848 A1* | 5/2004 | Michelson | 623/17.11 |
| 2004/0176853 A1* | 9/2004 | Sennett et al. | 623/17.16 |
| 2004/0210314 A1 | 10/2004 | Michelson | |
| 2004/0225360 A1* | 11/2004 | Malone | 623/17.11 |
| 2004/0249466 A1* | 12/2004 | Liu et al. | 623/17.16 |
| 2005/0055098 A1 | 3/2005 | Zdeblick et al. | |
| 2005/0101960 A1* | 5/2005 | Fiere et al. | 606/72 |
| 2005/0113917 A1* | 5/2005 | Chae et al. | 623/17.11 |
| 2005/0216083 A1* | 9/2005 | Michelson | 623/17.11 |
| 2006/0200149 A1* | 9/2006 | Hoy et al. | 606/72 |

FOREIGN PATENT DOCUMENTS

| | | |
|---|---|---|
| FR | 2850563 A1 | 8/2004 |

* cited by examiner

SPINAL IMPLANT

BACKGROUND

Current spinal devices have disadvantages relating to their fixation to a vertebral member and their ability to be revised, or removed, after their implantation. For instance, current devices may have special contours that need to be machined into the vertebrae, or may require special machining of the vertebrae and/or special implantation instrumentation to accommodate spikes, fins, or other structures. Additionally, current spinal devices may include surfaces encouraging hard or soft tissue in-growth. This in-growth makes it difficult to revise the implant.

Similarly, the associated revision instruments and methods have a number of disadvantages relating to their complexity or to their suitability for use in more sensitive areas of the spine. For instance, some revision systems require the use of many different instruments and devices to prepare the disc space and properly remove the device. Further, some revision systems rely on impacting, or hammering, away the in-growth on the implant. Such impaction techniques may be suitable in certain areas of the spine, but are not as desirable in other areas of the spine where the proximity of the spinal cord and nerve roots would favor more delicate procedures.

SUMMARY

The present invention relates to embodiments for a spinal implant having elements that are accessible by a surgical approach and releasably engagable by a surgical tool for improved revision of the spinal implant about a patient's spine.

In one embodiment the implant includes a main body having an attachment member. The attachment member provides a means for gripping the device for removal or repositioning.

DETAILED DESCRIPTION

The present invention relates to embodiments for a spinal implant 10 having an attachment member 24 that is accessible by a surgical approach. The attachment member 24 is releasably engagable by a surgical tool 60 for improved revision of the spinal implant 10 about a patient's spine.

Figure 1:
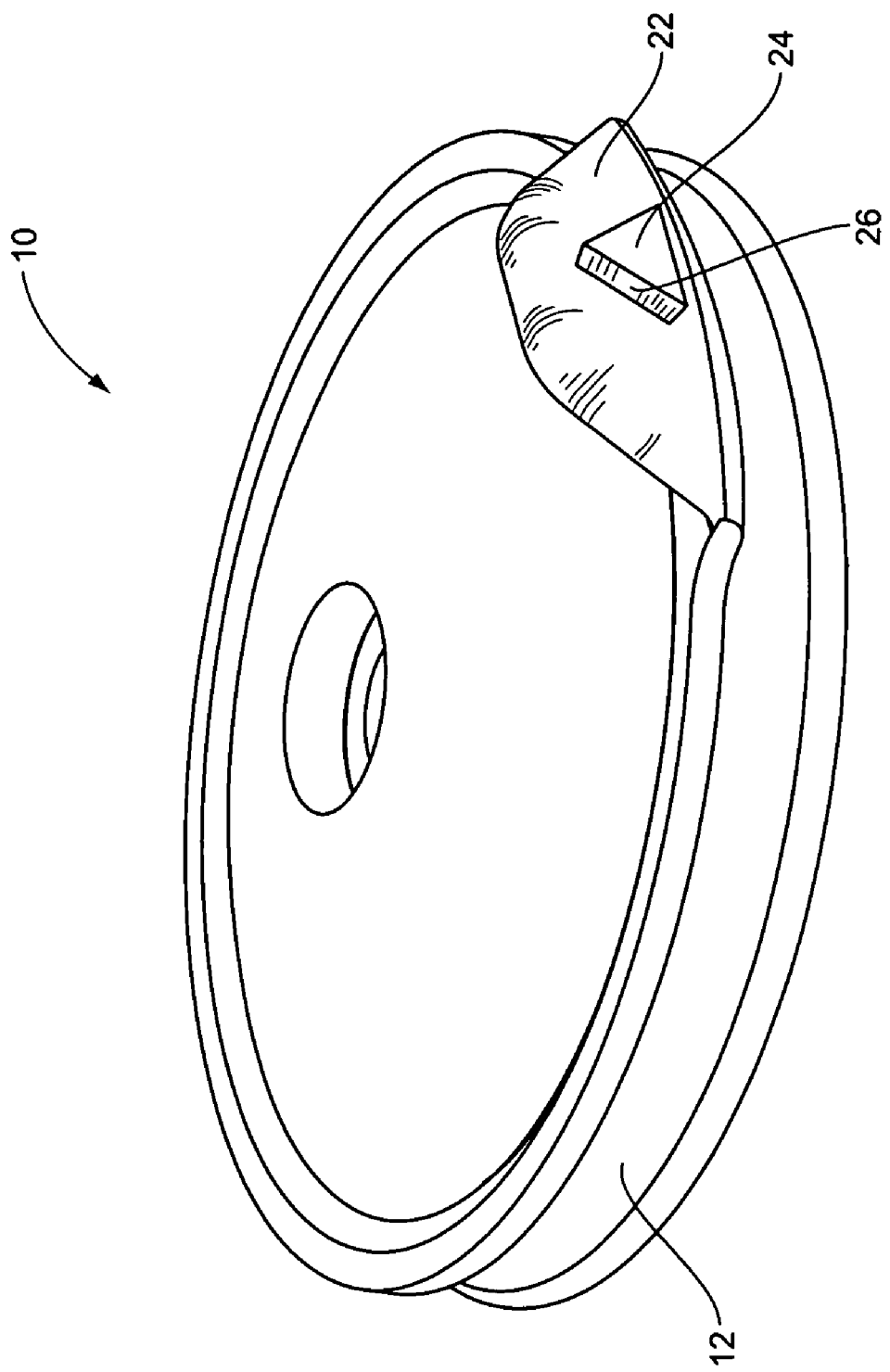
FIG. 1 is a perspective view illustrating a spinal implant according to one embodiment of the present invention.

FIG. 1 illustrates one embodiment of the implant 10 comprising a body 12 sized to fit between vertebral members. A flange 22 is affixed to the main body 12 and extends away from the main body. The flange 22 may be positioned at a variety of locations about the main body 12. The flange 22 is sized and positioned to be accessible during a surgical procedure when the main body 12 is positioned between the vertebral members. An attachment member 24 is positioned on the flange 22 for attachment of a tool for revising the implant 10. The attachment member 24 should be constructed in a manner to receive a tool, yet prevent in-growth that may obstruct the member 24 and prevent attachment.

The embodiment of FIG. 1 illustrates the attachment member 24 being a projection 24 that extends outward from the flange 22. The projection 24 has side walls 26 that provide at least one grip surface for a surgical tool 60. The side walls 26 may be substantially planar, or may be curved. One or more of the side walls 26 may taper inward to facilitate connection with the tool. Further, the projection 24 may extend substantially straight outward from the flange 22, or may extend outward at an angle. In one embodiment, the side walls 26 may be externally threaded for threaded engagement with a surgical tool 60. The projection 24 may have a variety of shapes and sizes, such as having a polygonal or circular cross-sectional shape.

Figure 2:
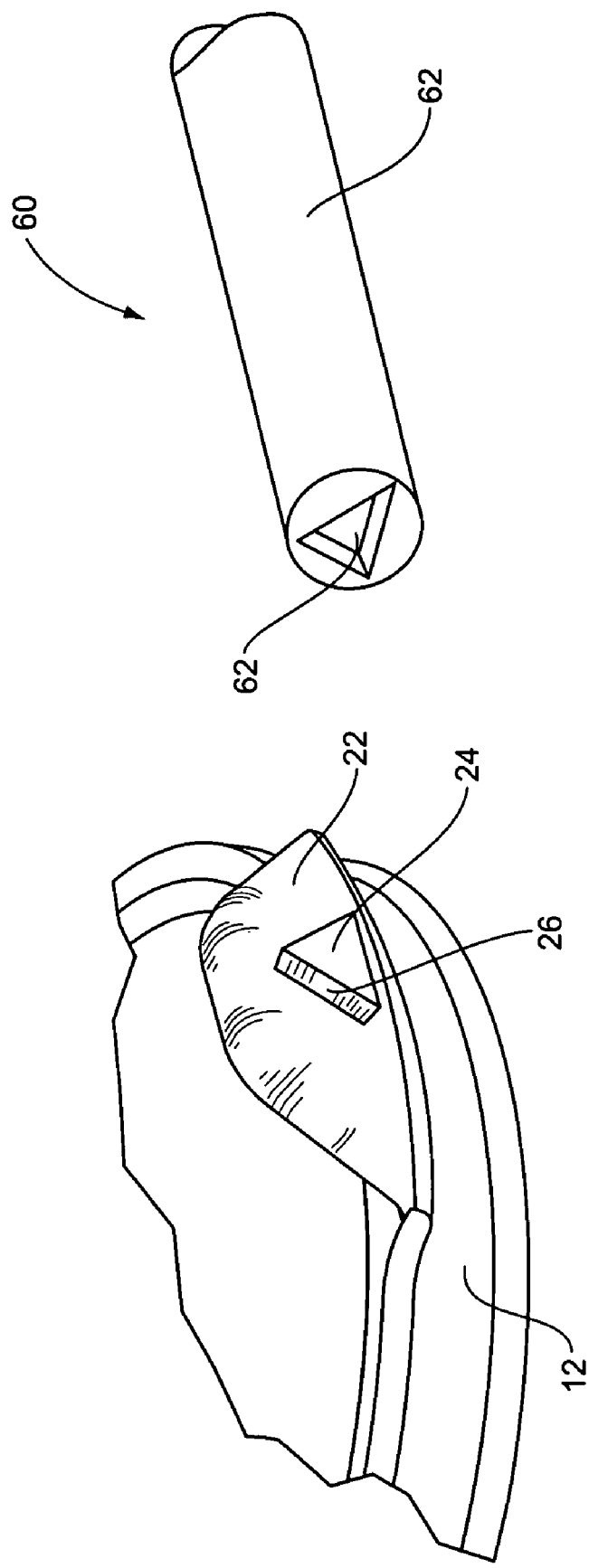
FIG. 2 is a partial perspective view of the surgical tool that attaches to an attachment member according to one embodiment of the present invention.

FIG. 2 illustrates an embodiment of the surgical tool 60 having an elongated body 64 and a distal end with a receiver 62. The receiver 62 has a shape that conforms with and is sized to extend over the projection 24. The tool 60 is operable between an open orientation for positioning the receiver 62 on the projection 24, and a closed orientation with the receiver 62 attached to the projection 24. In one embodiment, tool 60 is adjustable to reduce the size of the receiver 62 to apply a compressive force to the side walls 26 for attachment with the projection 24.

Figure 3:
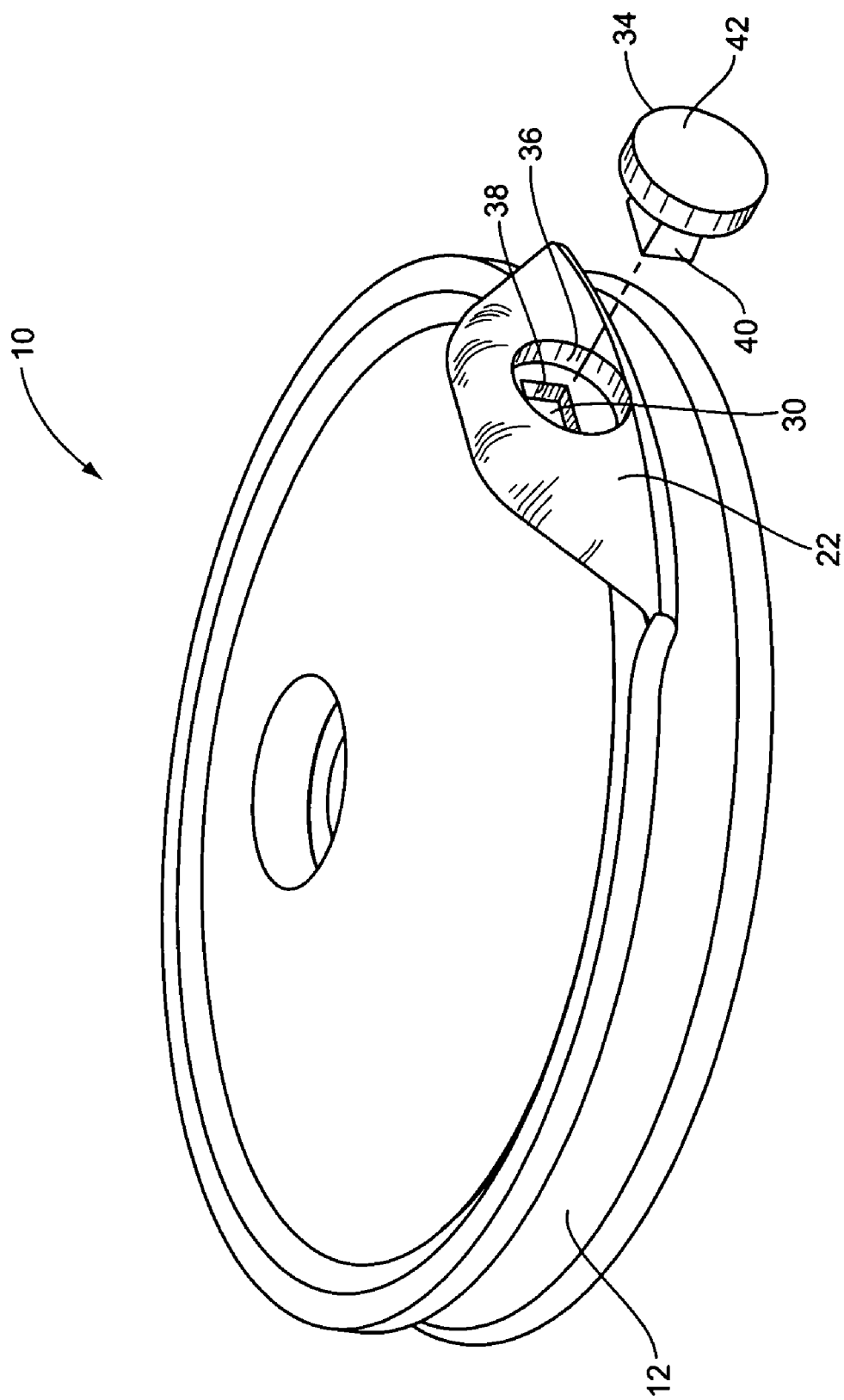
FIG. 3 is an exploded perspective view illustrating a spinal implant according to one embodiment of the present invention.

FIG. 3 illustrates another embodiment of the implant 10 with the flange 22 having an opening 30 having an interior wall that is releasably engaged by the surgical tool 60. The opening 30 may have a variety of shapes and sizes, such as circular or polygonal. Further, the cross-sectional diameter of the opening 30 may increase or decrease approaching the main body of the implant 10. The inner edges of the opening 30 may be smooth, threaded, or roughened to facilitate attachment as necessary. The opening 30 may extend completely through the flange 22, or may extend a distance less than the flange thickness. The surgical tool 60 may releasably engage the opening 30 by expanding against and engaging one or more of the interior walls. In the embodiment of a through-opening, the surgical tool 60 may extend through the opening 30 and engage a rear portion of the flange 22.

A plug 34 is removably securable in the opening 30 for preventing in-growth into the opening 30 after insertion of the implant 10. If left open, surrounding bone or soft tissue may grow into the opening 30 which may make it difficult to revise without surgical removal of the in growth. Closure of the opening 30 with the plug 34 prevents the surrounding hard and soft tissue from growing into the opening 30. In one embodiment, the plug 34 has a length to fit into and fill the opening, but is not so long as to extend into the vertebral member. In one embodiment, the plug has a length less than the thickness of the flange 22.

Typically the plug 34 is inserted into the opening 30 after the implant 10 has been inserted into the patient. The opening 30 may be used for an insertion tool to accurately locate the implant 10 during a first surgical event. After insertion, the plug 34 is inserted into the opening 30. During the revision surgical event, the plug 34 is removed from the opening 30 presenting a tissue free engagement surface for a surgical tool 60 to attach to the implant 10. Surgical removal of ingrown surrounding tissue should not be required, reducing surgical involvement and duration.

Figure 4:
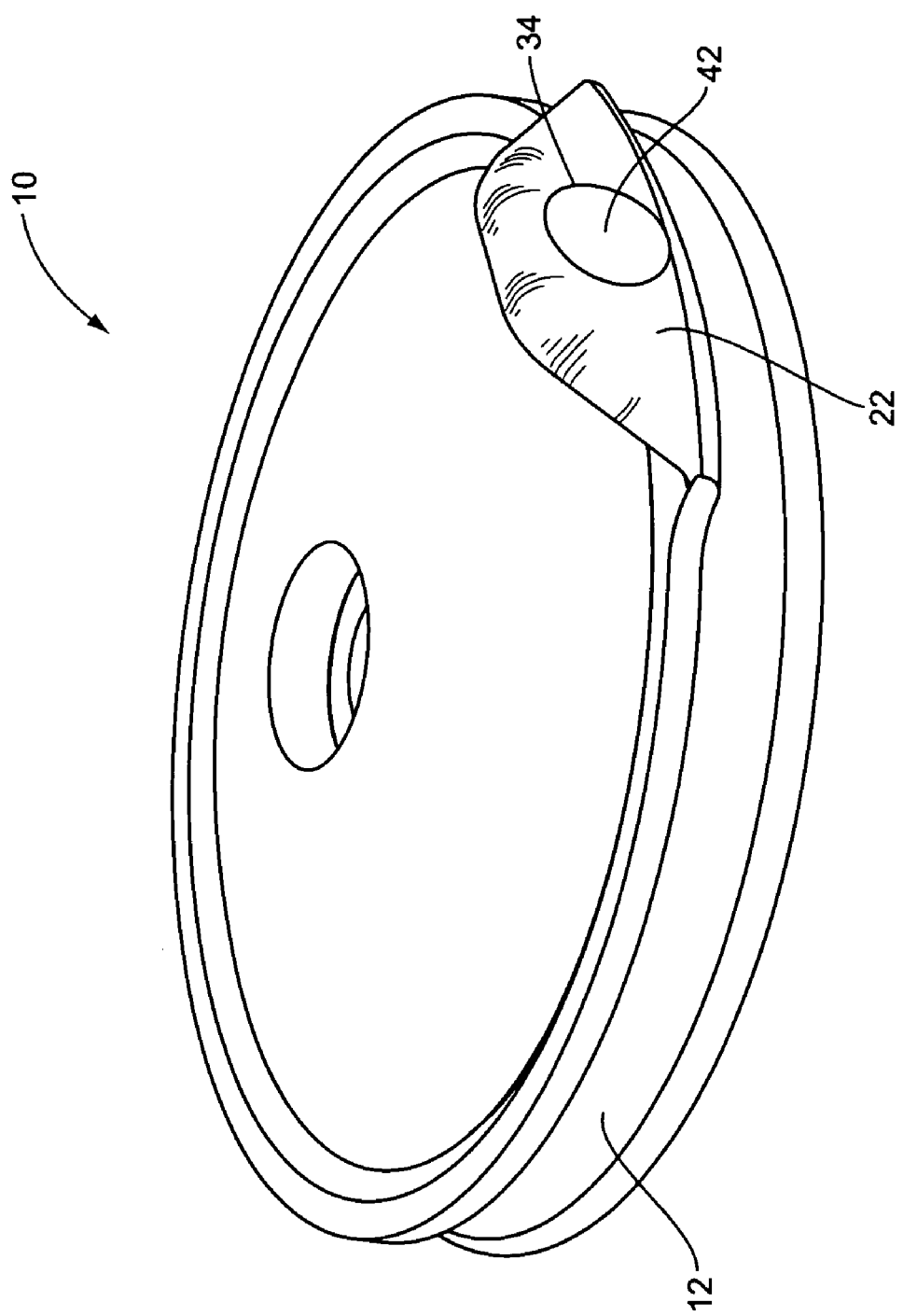
FIG. 4 is a perspective view illustrating a spinal implant according to one embodiment of the present invention.

As described above, the opening 30 may have various shapes and sizes. The plug 34 may correspondingly have various complementary shapes and sizes to be securely received in the opening 30. The opening 30 may also have two different cross-sectional shapes. In this embodiment the plug 34 may also correspond to the different cross-sectional shapes to be securely received in the opening 30. With reference to FIGS. 3 and 4, the opening 30 may include a first polygonal cross-sectional shape 38 and a second circular cross-sectional shape 36. In this embodiment, the first polygonal cross-section 38 extends distally in a direction generally opposite the insertion direction of the implant and terminates in a second circular cross-section 38. The plug 34 may be correspondingly configured with a polygonal plug shaft 40 affixed to a circular plug head 42 sized to be removably securable within their corresponding opening cross-section 36, 38. The polygonal plug shaft 40 passes through the second circular cross-section 38 and is securably received by the first polygonal cross-section 38. The circular plug head 42 is securably received by the second circular cross-section 36. The second circular cross-section 36 may be countersunk permitting the circular plug head 42 to fit flush with the flange 22 or main body 12 when inserted into the opening 30.

Figure 5:
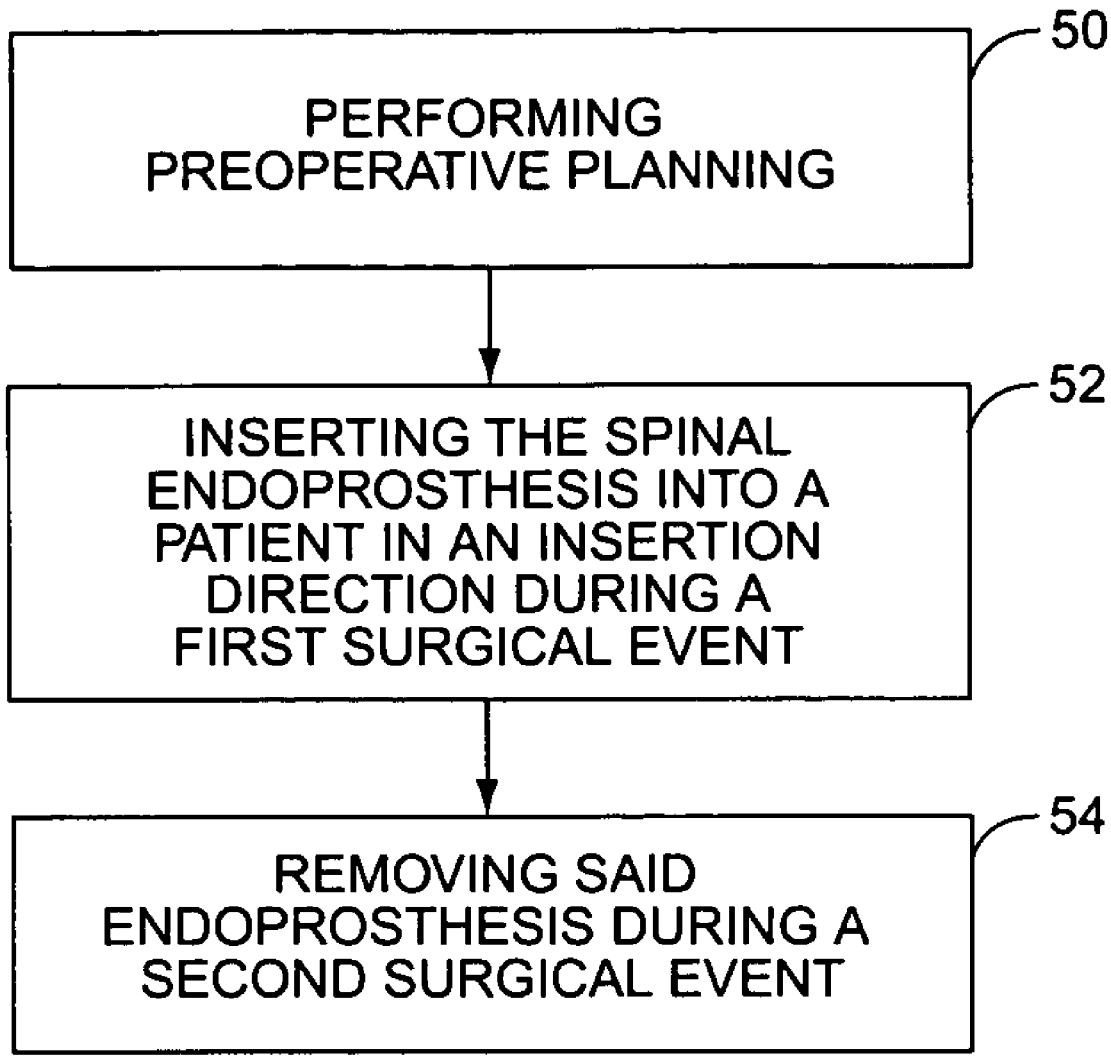
FIG. 5 is a schematic flow diagram illustrating the process of revising the spinal implant according to one embodiment of the present invention.

With reference to FIG. 5, a method of revising the spinal implant 10 is illustrated. Initially, pre-operative planning is performed (Step 50). This step may include examining the patient, taking x-rays or performing other diagnostic procedures to analyze the spine, analyzing and/or calculating the existing or natural range of motion of the spinal motion segment, and/or measuring the natural spine to determine an appropriate size spinal implant. Pre-operative planning may further include determining the type of implant 10 to be inserted, determining the spinal insertion site of the implant 10, the surgical approach required to access the spinal insertion site, and determining an insertion direction of the implant 10.

Next, the implant 10 is inserted into the patient during a first surgical event (Step 52). This may include removing all or a portion of a spinal segment, preparing the spine for receiving the spinal implant 10 such as by machining or contouring the adjacent spinal segments to receive the implant 10, and inserting the implant 10 in an insertion direction into the prepared spinal space until it reaches a predetermined desired position. Securing the implant 10 may occur naturally due to the compressive forces acting across the implant 10, may occur due to the contouring of the adjacent spinal segments, may occur due to supplemental fixation techniques such as applying a screw or other separate component to hold a component of the implant 10 to the vertebral member, or may occur as some combination of these techniques.

Finally, the implant 10 is revised during a second surgical event (Step 54). This may include performing preoperative planning similar to that described above in step 50. Once prepared, the surgical tool 60 is inserted into the patient and attached to the attachment member 24. In a projection embodiment, the tool 60 may be directly connected with the member 24. In an embodiment having an opening 30, the plug 34 is initially removed and then the tool 60 is attached to the opening 30. Once the tool 60 is attached, the implant 10 may be completely removed from the patient, adjusted to a new position, or other.

While the implant 10 has been described above as having the attachment member 24 affixed to the flange 22, other designs are also contemplated. The attachment member 24 may be positioned directly on the body 12. In this design, the implant 10 may or may not include a flange 22. In one embodiment, an opening is positioned within the body 12. The opening has side walls and a back wall as it does not extend entirely through the body 12.

Multiple attachment members 24 may be positioned about the implant 10. The multiple positions facilitate a variety of approach directions for inserting and revising the implant 10. In these embodiments, each of the attachment members 24 may have the same configuration (e.g., projection, opening), or they may have a combination of both.

Surgical approaches to spine fall within three broad categories of posterior approaches, anterior approaches and lateral or midline approaches. Within each broad category of approach there are numerous specific approaches tailored specifically for the cervical, thoracic, lumbar, sacral or coccygeal segment of the spine to be surgically accessed. The implant 10 may be inserted or revised about a patient's spine by any of the posterior, anterior or lateral spinal surgical approaches.

Figure 6:
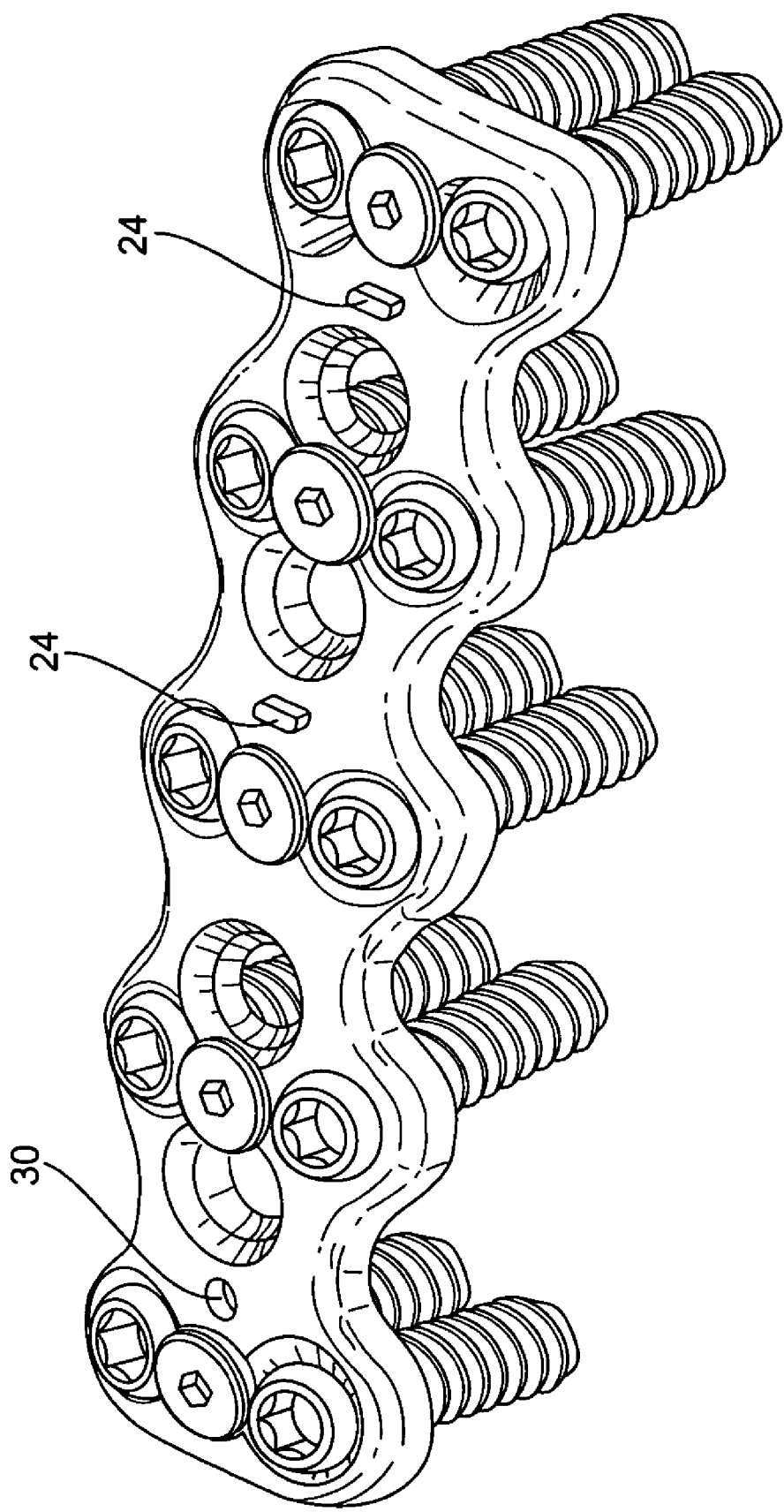
FIG. 6 is a perspective view of a spinal implant according to one embodiment of the present invention.

The attachment member 24 may be positioned on a variety of different implants 10. The embodiments of FIGS. 1-4 illustrate an intervertebral design that is inserted at least partially between vertebral members. One specific design is described in U.S. Patent Pub. No. 2002/0128715, the disclosure of which is incorporated herein by reference. The implant 10 may also include other types of spinal devices. FIG. 6 illustrates a plate that attaches to the surface of the vertebral members. In this embodiment, multiple attachment members 24 are positioned about the plate in locations to be accessible to the surgical tool 60. The attachment members 24 include both projections 24 and openings 30.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:
1. A spinal implant comprising:
a body;
an opening in the body that includes an inlet and a closed bottom opposite from the inlet, the opening comprising first and second opening sections each located a different distance from the inlet and a longitudinal axis that extends through the opening and the inlet and the bottom, said first opening section in closer proximity to the inlet than the second opening section and having a first back wall and one or more first sidewalls that define a first cross-sectional shape, the first opening section including a first width measured perpendicular to the longitudinal axis between the one or more first sidewalls, said second opening section disposed in the first back wall and having the closed bottom and one or more second sidewalls that define a different second cross-sectional shape, the second opening section including a second width measured perpendicular to the longitudinal axis between the one or more second sidewalls, the opening being positioned to be accessible by a surgical approach and releasably engagable by a surgical tool, the second width being smaller than the first width, wherein one of the first and second cross-sectional shapes is polygonal; and
a plug removably securable in the opening, the plug closing the opening to prevent tissue growth into the opening; the plug including a distal end positioned adjacent to and facing the closed bottom when secured in the opening.

2. The implant of claim 1, wherein the first opening section has a first fixed cross-sectional width, and the second opening section has a different second fixed cross-sectional width.

3. A spinal implant comprising:
a body having an outwardly-extending flange;
a first opening positioned in the flange and having a back wall and a first cross-sectional shape and size defined by one or more first sidewalls, the first opening having a first width measured between the one or more first sidewalls;
a second opening disposed in the back wall of the first opening, said second opening having a different second cross-sectional shape and size defined by one or more second sidewalls, the second opening having a second width measured between the one or more second sidewalls that is smaller than the first width;
the sidewalls of the first and second openings and a back wall of the second opening each being solid to isolate an interior space formed within the first and second openings to prevent tissue growth into the first and second openings;
a non-threaded plug including a first longitudinal section with a third cross-sectional shape and size that complements the first cross-sectional shape and size and a second longitudinal section with a fourth cross-sectional shape and size that complements the second cross-sectional shape and size, the plug removably securable in said first and second openings.

4. The implant of claim 1, wherein the plug is non-threaded.

5. The implant of claim 3, wherein the back wall of the second opening is continuous between the one or more second sidewalls and forms an enclosed bottom.

6. The implant of claim 5, wherein the back wall is positioned in the flange and away from the body.

7. The implant of claim 3, wherein both the first cross-sectional shape of the first opening and the third cross-sectional shape of the plug are polygonal.

8. The implant of claim 3, wherein both the second cross-sectional shape of the second opening and the fourth cross-sectional shape of the plug are polygonal.

9. The implant of claim 3, wherein the first longitudinal section includes a greater width than the second longitudinal section.

* * * * *